United States Patent
Schulz (10) Patent No.: US 7,162,125 B1
(45) Date of Patent: Jan. 9, 2007

(54) OPTIMIZED GRATING BASED BIOSENSOR AND SUBSTRATE COMBINATION

(75) Inventor: Stephen Schulz, Lee, NH (US)

(73) Assignee: SRU Biosystems, Inc., Woburn, MA (US)

(*) Notice: Subject to any disclaimer, the term of this patent is extended or adjusted under 35 U.S.C. 154(b) by 0 days.

(21) Appl. No.: 11/207,442

(22) Filed: Aug. 18, 2005

Related U.S. Application Data (60) Provisional application No. 60/693,680, filed on Jun. 23, 2005.

(51) Int. Cl.
*G02B 6/34* (2006.01)
*G02B 6/26* (2006.01)
*C12Q 1/68* (2006.01)
*C12M 1/34* (2006.01)

(52) U.S. Cl. .................... 385/37; 385/12; 385/147; 435/6; 435/288.7

(58) Field of Classification Search ............ 385/12–15, 385/147, 37; 435/288.7, 6
See application file for complete search history.

(56) References Cited

U.S. PATENT DOCUMENTS

| | | | | |
|---|---|---|---|---|
| 5,640,239 | A * | 6/1997 | Takamiya et al. | 356/486 |
| 6,618,116 | B1 * | 9/2003 | Murata et al. | 349/201 |
| 6,665,070 | B1 * | 12/2003 | Yarussi et al. | 356/369 |
| 2002/0127565 | A1 * | 9/2002 | Cunningham et al. | 435/6 |
| 2003/0017581 | A1 | 1/2003 | Li et al. | 435/287.2 |
| 2003/0027327 | A1 | 2/2003 | Cunningham et al. | 435/287.2 |
| 2003/0032039 | A1 | 2/2003 | Cunningham et al. | 435/6 |
| 2003/0059855 | A1 | 3/2003 | Cunningham et al. | 435/7.9 |
| 2003/0077660 | A1 | 4/2003 | Pien et al. | 435/71 |

OTHER PUBLICATIONS

Cunningham, B.T., P. Li, B. Lin, and J. Pepper, *Colorimetric resonant reflection as a direct biochemical assay technique.* Sensors and Actuators B, 2002. 81: p. 316-328.

Cunningham, B.T., J. Qiu, P. Li, J. Pepper, and B. Hugh, *A plastic colorimetric resonant optical biosensor for multiparallel detection of label-free biochemical interactions,* Sensors and Actuators B, 2002. 85: p. 219-226.

(Continued)

*Primary Examiner*—John D. Lee
(74) *Attorney, Agent, or Firm*—McDonnell Boehnen Hulbert & Berghoff LLP (57) ABSTRACT

A grating-based biosensor is disclosed where the biosensor is constructed and arranged such that the grating lines of the sensor align with an optical axis of a birefringent substrate, so as to improve resonance peak uniformity. Methods of manufacturing biosensors to provide alignment of the grating lines with the optical axes of a birefringent substrate are also disclosed. One embodiment uses a grating master wafer to form a grating on a continuous web of substrate material. The grating master wafer is rotated relative to the web until the lines of the grating in the master wafer are in substantial alignment with the optical axis of the web. A UV curable material is applied to the wafer and cured in place to form the grating on the surface of the substrate web. With a web of some preferred materials, such as PET film, one need only determine the optical axis orientation once for a given web since the optical axis orientation is essentially constant along the length of the web.

13 Claims, 3 Drawing Sheets

OTHER PUBLICATIONS

Haes, A.J. and R.P.V. Duyne, *A Nanoscale Optical Biosensor: Sensitivity and Selectivity of an Approach Based on the Localized Surface Plasmon Resonance Spectroscopy of Triangular Silver Nanoparticles*. Journal of the American Chemical Society, 2002. 124: p. 10596-10604.

Li, P., B. Lin, J. Gerstenmaier, and B.T. Cunningham, *A new method for label-free imaging of biomolecular interactions*. Sensors and Actuators B, 2003.

* cited by examiner

ROW A OF A 96 WELL BIND™ MICROPLATE WHERE THE GRATING AND SUBSTRATE
OPTICAL AXES HAVE ~25 DEGREES SEPARATION..
THE FIXED POLARIZER ALIGNS WITH THE GRATING

Fig. 5

ROW A OF A 96 WELL BIND™ MICROPLATE WHERE THE GRATING AND SUBSTRATE
OPTICAL AXES HAVE ~2 DEGREES SEPARATION - ACCORDING TO THE INVENTION.
THE FIXED POLARIZER ALIGNS WITH THE GRATING

OPTIMIZED GRATING BASED BIOSENSOR AND SUBSTRATE COMBINATION

CROSS-REFERENCE TO RELATED APPLICATION

This application claims priority benefits under 35 U.S.C. § 119(e) of U.S. Provisional application Ser. No. 60/693,680 filed Jun. 23, 2005, the entire content of which is incorporated by reference herein.

BACKGROUND

A. Field of the Invention

This invention relates generally to grating-based biochemical sensor devices, and methods of manufacture of such devices. Such devices are typically based on photonic crystal technology and are used for optical detection of the adsorption of a biological material, such as DNA, protein, viruses or cells, or chemicals, onto a surface of the device or within a volume of the device.

B. Description of Related Art

Grating-based biosensors represent a new class of optical devices that have been enabled by recent advances in semiconductor fabrication tools with the ability to accurately deposit and etch materials with precision less than 100 nm.

Several properties of photonic crystals make them ideal candidates for application as grating-type optical biosensors. First, the reflectance/transmittance behavior of a photonic crystal can be readily manipulated by the adsorption of biological material such as proteins, DNA, cells, virus particles, and bacteria. Each of these types of material has demonstrated the ability to alter the optical path length of light passing through them by virtue of their finite dielectric permittivity. Second, the reflected/transmitted spectra of photonic crystals can be extremely narrow, enabling high-resolution determination of shifts in their optical properties due to biochemical binding while using simple illumination and detection apparatus. Third, photonic crystal structures can be designed to highly localize electromagnetic field propagation, so that a single photonic crystal surface can be used to support, in parallel, the measurement of a large number of biochemical binding events without optical interference between neighboring regions within <3–5 microns. Finally, a wide range of materials and fabrication methods can be employed to build practical photonic crystal devices with high surface/volume ratios, and the capability for concentrating the electromagnetic field intensity in regions in contact with a biochemical test sample. The materials and fabrication methods can be selected to optimize high-volume manufacturing using plastic-based materials or high-sensitivity performance using semiconductor materials.

Representative examples of grating-type biosensors in the prior art are disclosed in Cunningham, B. T., P. Li, B. Lin, and J. Pepper, *Colorimetric resonant reflection as a direct biochemical assay technique.* Sensors and Actuators B, 2002. 81: p. 316–328; Cunningham, B. T., J. Qiu, P. Li, J. Pepper, and B. Hugh, *A plastic calorimetric resonant optical biosensor for multiparallel detection of label-free biochemical interactions*, Sensors and Actuators B, 2002. 85: p. 219–226; Haes, A. J. and R. P. V. Duyne, *A Nanoscale Optical Biosensor: Sensitivity and Selectivity of an Approach Based on the Localized Surface Plasmon Resonance Spectroscopy of Triangular Silver Nanoparticles.* Journal of the American Chemical Society, 2002. 124: p. 10596–10604.

The combined advantages of photonic crystal biosensors may not be exceeded by any other label-free biosensor technique. The development of highly sensitive, miniature, low cost, highly parallel biosensors and simple, miniature, and rugged readout instrumentation will enable biosensors to be applied in the fields of pharmaceutical discovery, diagnostic testing, environmental testing, and food safety in applications that have not been economically feasible in the past.

In order to adapt a photonic bandgap device to perform as a biosensor, some portion of the structure must be in contact with a liquid test sample. Biomolecules, cells, proteins, or other substances are introduced to the portion of the photonic crystal and adsorbed where the locally confined electromagnetic field intensity is greatest. As a result, the resonant coupling of light into the crystal is modified, and the reflected/transmitted output (i.e., peak wavelength) is tuned, i.e., shifted. The amount of shift in the reflected output is related to the amount of substance present on the sensor. The sensors are used in conjunction with an illumination and detection instrument that directs polarized light into the sensor and captures the reflected or transmitted light. The reflected or transmitted light is fed to a spectrometer that measures the shift in the peak wavelength.

The ability of photonic crystals to provide high quality factor (Q) resonant light coupling, high electromagnetic energy density, and tight optical confinement can also be exploited to produce highly sensitive biochemical sensors. Here, Q is a measure of the sharpness of the peak wavelength at the resonant frequency. Photonic crystal biosensors are designed to allow a liquid test sample to penetrate the periodic lattice, and to tune the resonant optical coupling condition through modification of the surface dielectric constant of the crystal through the attachment of biomolecules or cells. Due to the high Q of the resonance, and the strong interaction of coupled electromagnetic fields with surface-bound materials, several of the highest sensitivity biosensor devices reported are derived from photonic crystals. See the Cunningham et al. papers cited previously. Such devices have demonstrated the capability for detecting molecules with molecular weights less than 200 Daltons (Da) with high signal-to-noise margins, and for detecting individual cells. Because resonantly-coupled light within a photonic crystal can be effectively spatially confined, a photonic crystal surface is capable of supporting large numbers of simultaneous biochemical assays in an array format, where neighboring regions within ~10 µm of each other can be measured independently. See Li, P., B. Lin, J. Gerstenmaier, and B. T. Cunningham, *A new method for label-free imaging of biomolecular interactions*. Sensors and Actuators B, 2003.

There are many practical benefits for biosensors based on photonic crystal structures. Direct detection of biochemical and cellular binding without the use of a fluorophore, radioligand or secondary reporter removes experimental uncertainty induced by the effect of the label on molecular conformation, blocking of active binding epitopes, steric hindrance, inaccessibility of the labeling site, or the inability to find an appropriate label that functions equivalently for all molecules in an experiment. Label-free detection methods greatly simplify the time and effort required for assay development, while removing experimental artifacts from quenching, shelf life, and background fluorescence. Compared to other label-free optical biosensors, photonic crystals are easily queried by simply illuminating at normal incidence with a broadband light source (such as a light bulb or LED) and measuring shifts in the reflected color. The simple excitation/readout scheme enables low cost, miniature, robust systems that are suitable for use in laboratory instruments as well as portable handheld systems for point-of-care medical diagnostics and environmental monitoring. Because the photonic crystal itself consumes no power, the devices are easily embedded within a variety of liquid or gas sampling systems, or deployed in the context of an optical network where a single illumination/detection base station can track the status of thousands of sensors within a building. While photonic crystal biosensors can be fabricated using a wide variety of materials and methods, high sensitivity structures have been demonstrated using plastic-based processes that can be performed on continuous sheets of film. Plastic-based designs and manufacturing methods will enable photonic crystal biosensors to be used in applications where low cost/assay is required, that have not been previously economically feasible for other optical biosensors.

The assignee of the present invention has developed a photonic crystal biosensor and associated detection instrument. The sensor and detection instrument are described in the patent literature; see U.S. patent application publications U.S. 2003/0027327; 2002/0127565, 2003/0059855 and 2003/0032039. Methods for detection of a shift in the resonant peak wavelength are taught in U.S. Patent application publication 2003/0077660. The biosensor described in these references include 1- and 2-dimensional periodic structured surfaces applied to a continuous sheet of plastic film or substrate. The crystal resonant wavelength is determined by measuring the peak reflectivity at normal incidence with a spectrometer to obtain a wavelength resolution of 0.5 picometer. The resulting mass detection sensitivity of <1 pg/mm$^2$ (obtained without 3-dimensional hydrogel surface chemistry) has not been demonstrated by any other commercially available biosensor.

Figure 1:
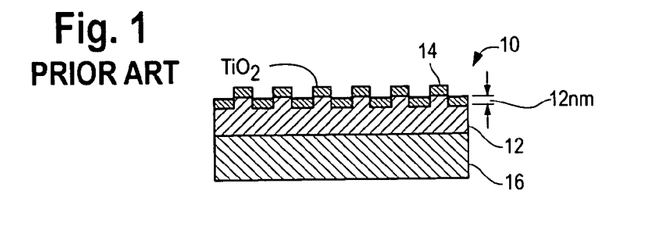
FIG. 1 is an illustration of a prior art biosensor arrangement.

A fundamental advantage of the biosensor devices described in the above-referenced patent applications is the ability to mass-manufacture with plastic materials in continuous processes at a 1–2 feet/minute rate. Methods of mass production of the sensors are disclosed in U.S. Patent application publication 2003/0017581. As shown in FIG. 1, the periodic surface structure of a biosensor 10 is fabricated from a low refractive index material 12 that is overcoated with a thin film of higher refractive index material 14. The low refractive index material 12 is bonded to a substrate 16. The surface structure is replicated within a layer of cured epoxy 12 from a silicon-wafer "master" mold (i.e. a negative of the desired replicated structure) using a continuous-film process on a polyester substrate 16. The liquid epoxy 12 conforms to the shape of the master grating, and is subsequently cured by exposure to ultraviolet light. The cured epoxy 12 preferentially adheres to the polyester substrate sheet 16, and is peeled away from the silicon wafer. Sensor fabrication was completed by sputter deposition of 120 nm titanium oxide (TiO$_2$) high index of refraction material 14 on the cured epoxy 12 grating surface. Following titanium oxide deposition, 3×5-inch microplate sections are cut from the sensor sheet, and attached to the bottoms of bottomless 96-well and 384-well microtiter plates with epoxy.

Figure 2:
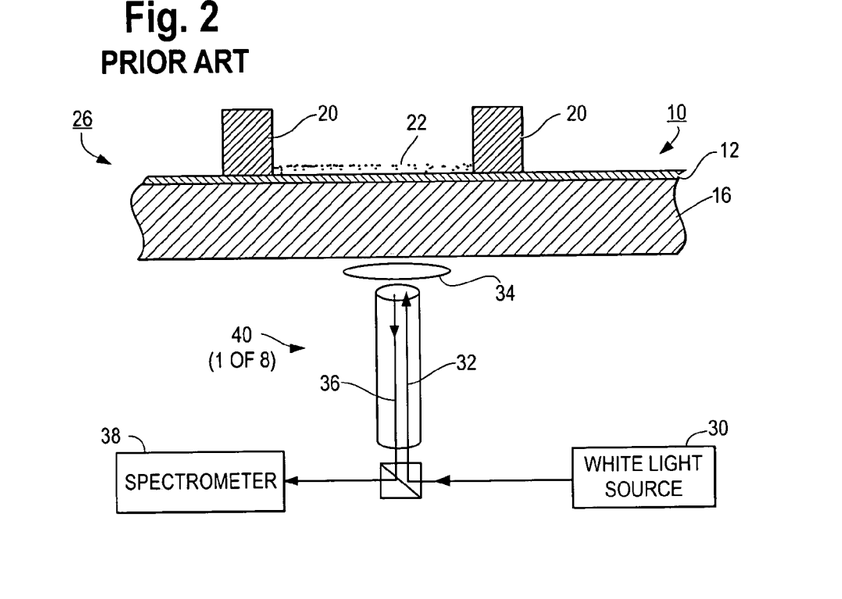
FIG. 2 is an illustration of a prior art biosensor and detection system for illuminating the biosensor and measuring shifts in the peak wavelength of reflected light from the biosensor.

As shown in FIG. 2, the wells 20 defining the wells of the mircotiter plate contain a liquid sample 22. The combination of the bottomless microplate and the biosensor structure 10 is collectively shown as biosensor apparatus 26. Using this approach, photonic crystal sensors are mass produced on a square-yardage basis at very low cost.

Figure 3:
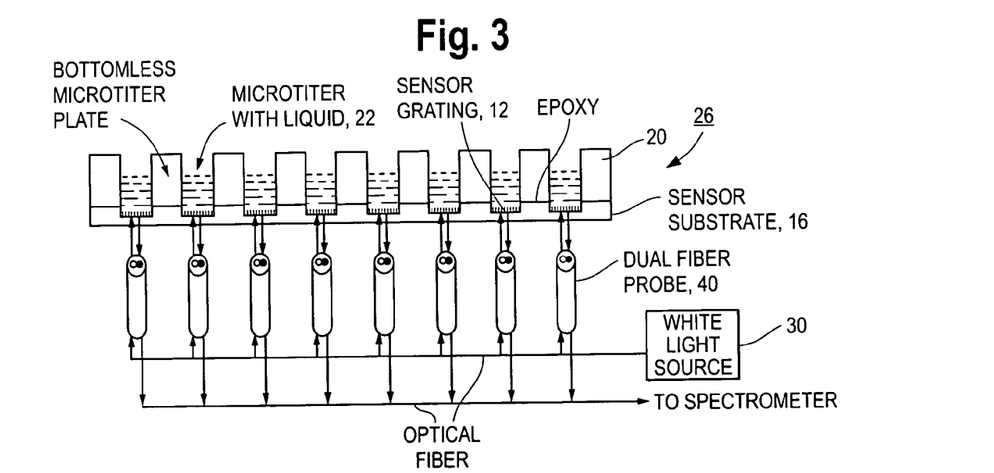
FIG. 3 is an illustration of an arrangement of 8 illumination heads that read an entire row of wells of a biosensor device comprising the structure of FIG. 1 affixed to the bottom of bottomless microtiter plate.

The detection instrument for the photonic crystal biosensor is simple, inexpensive, low power, and robust. A schematic diagram of the system is shown in FIG. 2. In order to detect the reflected resonance, a white light source illuminates a ~1 mm diameter region of the sensor surface through a 100 micrometer diameter fiber optic 32 and a collimating lens 34 at nominally normal incidence through the bottom of the microplate. A detection fiber 36 is bundled with the illumination fiber 32 for gathering reflected light for analysis with a spectrometer 38. A series of 8 illumination/detection heads 40 are arranged in a linear fashion, so that reflection spectra are gathered from all 8 wells in a microplate column at once. See FIG. 3. The microplate+biosensor 10 sits upon a X-Y addressable motion stage (not shown in FIG. 2) so that each column of wells in the microplate can be addressed in sequence. The instrument measures all 96 wells in ~15 seconds, limited by the rate of the motion stage. Further details on the construction of the system of FIGS. 2 and 3 are set forth in the published U.S. Patent Application 2003/0059855.

All of the previously cited art is fully incorporated by reference herein.

SUMMARY

A grating-based biosensor is disclosed where the biosensor is constructed and arranged such that the lines of the grating are aligned with one of the optical axes of a substrate sheet (e.g., PET film), so as to improve resonance peak uniformity. Such alignment is maintained during the biosensor fabrication, for example by rotating a grating master wafer relative to the axis of the web of substrate material, and then forming the grating on the surface of the substrate web using the master such that the grating lines are in alignment with an optical axis of the substrate. The operator measures substrate optical axis orientation prior to the beginning of grating replication and then rotates the grating master wafer so as to align the grating with the optical axis.

With a biosensor constructed in this configuration, light with polarization important to the resonance phenomenon will not undergo significant phase shift as it travels to or from the grating. Such a biosensor has uniform and reliable resonance peak quality.

In one embodiment, a biosensor is provided comprising a substrate, such as a birefringent clear polymer film. One preferred film is PET, however other selections are possible. The substrate, which may be a birefringent film, comprises a material having an optical axis. A grating is applied to the substrate. The grating comprises features arranged in a plurality of parallel lines and wherein the lines of the grating are in substantial alignment with the optical axis of the substrate.

Methods of manufacturing biosensors to provide alignment of the grating lines with the optical axes of a birefringent substrate are also disclosed.

In one embodiment, a method of manufacturing a biosensor is provided comprising the steps of:

a) feeding a web of substrate material to a station, the web of substrate material having an optical axis;

b) applying a grating to the substrate material at the station, wherein the grating comprises a plurality of parallel lines; and wherein, in the performance of step (b), the grating is applied to the substrate in a manner whereby the lines of the grating are in substantial alignment with the optical axis of the web of substrate material.

In another embodiment, a method is provided of manufacturing a biosensor which provides for continuous production of a biosensor. The method comprises the steps of:

a) providing a continuous web of substrate material;

b) determining the orientation of an optical axis in the web of substrate material;

c) providing a grating master wafer having a plurality of parallel lines;

d) orienting the grating master wafer relative to the web of substrate material such that the lines of the grating master wafer are in substantial alignment with the optical axis;

e) forming a grating on the web of material using the grating master wafer; and f) advancing the web of substrate material relative to the grating master wafer and repeating step e).

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DETAILED DESCRIPTION

This disclosure describes a grating-based biosensor where the grating lines of the sensor and the optical axes of the sensor's substrate are substantially aligned. In practice, they have a parallel or perpendicular orientation with respect to each other, typically within a few degrees of each other or preferably closer.

The biosensing technology described above in the background section relies on accurately determining the spectral wavelength at which resonance occurs when light reflects from the sensor's grating structure. Resonance manifests as a narrow spectral peak. The accuracy of peak position determination is proportional to the slope of the peak shape. Hence, narrow and tall peaks improve sensor sensitivity. This invention dramatically improves the lot-to-lot consistency and spatial uniformity of the biosensor's peak quality.

The detection instrument of the above-described published applications of the applicant's assignee exploits an optical resonance mode stimulated by light polarized with some vector component perpendicular to the grating lines. The resonance phenomenon reflects 100% of that component that has polarization perpendicular to the grating lines. The literature refers to this mode as the Transverse Magnetic (TM) mode. A TE mode exists, orthogonally to the TM mode, but it has a much broader and less useful resonance shape. A polarizer, in the instrument that interrogates the sensor, separates the sharp TM resonance peak from non-resonant, background light reflected at other polarizations.

To achieve maximum peak intensity, the optical axis of the instrument polarizer must align with the TM light reflected from the grating and/or polarized incident light should have TM polarization. Thus, in the ideal configuration, the polarizer axis aligns orthogonally to the grating lines. In its most versatile configuration, the detection instrument requires light to interrogate the sensor from the bottom, specifically the light travels twice through the sensor substrate. This invention allows the ideal polarization condition to hold, over the entire surface of the biosensor, while also allowing the use of a birefringent (polarization changing) substrate material.

The applicant's assignee has pioneered a low cost, polymer web based version of the resonant grating biosensor. The choice of PolyEthyleneTerephthalate (PET) polymer film as the substrate material (item 16 in FIG. 1) offers a number of advantages. For example, PET has relatively high mechanical strength (modulus), thermal stability (Tg), and chemical tolerance. Perhaps most importantly, for optical biosensing and a number of other technical applications, one can readily obtain PET with high optical clarity and quality at low cost. PET has one significant disadvantage with respect to use as a substrate for grating based biosensors. The two dimensional stretching, that occurs during PET manufacturing, results in a birefringent material. The magnitude of stretching and hence the magnitude of birefringence, varies across the width of the PET web manufacturing process. Stretching and birefringence remain constant along the length (machine direction) of the PET manufacturing process. This invention overcomes the problem of PET birefringence in the manufacture of biosensors.

Most introductory optics texts treat the subject of birefringence and birefringent materials. A brief summary is provided here, and the interested reader is directed to the textbooks for a more extensive analysis of the phenomenon.

A birefringent material has two optical axes. Polarized light, in a birefringent material, has two components traveling at different speeds. Light polarized along the high index, "slow" axis travels slower than light polarized perpendicularly along the fast axis. The refractive index (speed) difference along each axis then introduces a phase difference between the two components. The phase difference grows as the light travels further through the birefringent material. At any given substrate location, the exiting light has a composite polarization orientation and intensity that is a function of the phase difference and magnitude of the two components. In the case of PET film, these axes are approximately orthogonal to each other. The relationship below gives the phase difference in terms of number of wavelengths:

Phase difference in number of wavelengths=Dn*d/lambda where Dn represents the substrate's birefringence, the refractive index difference between the two optical axes of the substrate, d is thickness of substrate and lambda is wavelength of the light.

Equations for elliptical polarization generally describe the amplitude and orientation of light exiting a birefringent material.

The two substrate optical axes have a numerically small difference in refractive index (~0.05 for PET). However, over the optically large thickness of the substrate, the total lag between light components, traveling along each axis, translates to numerous wavelength periods. Small gradations in birefringence magnitude (Dn) or substrate thickness d across the substrate (the result of the PET manufacturing process) translate into large gradations in polarization state. High spatial variability of polarization orientation results in high variability in the biosensor's peak quality. This variability occurs spatially over the area of the biosensor and temporally with the use of different sections of the PET manufacturer's master roll.

In a principal aspect of this disclosure, the biosensor is constructed and arranged such that the alignment of the grating lines with one of the PET optical axes is specified, during the sensor fabrication. The alignment need not be exact, but ideally is as close as can be reasonably attained consistent with manufacturability and cost considerations. In this configuration, light with polarization important to the resonance phenomenon will not undergo significant phase shift as it travels to or from the grating. Such a biosensor has uniform and reliable resonance peak quality. To achieve such alignment, the operator in the manufacturing line measures the substrate optical axis orientation prior to the beginning of grating replication onto the substrate, and once this orientation is determined then rotates the grating master wafer to substantially align the grating formed in the substrate with the determined optical axis orientation.

Figure 4:
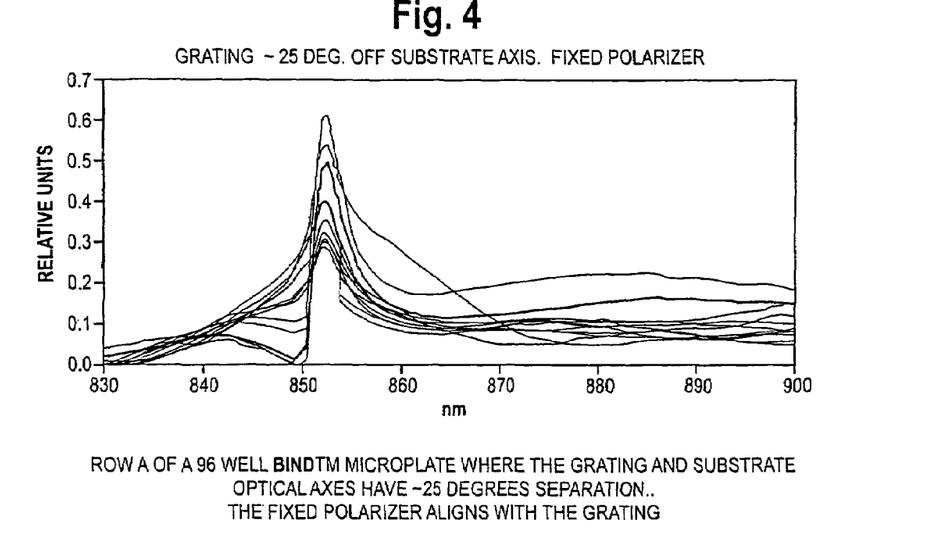
FIG. 4 shows a graph of measured illumination intensity (in relative units) as a function of wavelength for a row of 12 wells in a microtiter plate in the construction of FIG. 3 when a substance to be tested is present in the unit cells. Each line in the graph represents data for a separate well. A measured resonant frequency peak of 852 nm is observed in each of the wells. In this example, the grating and substrate optical axes have ~25 degrees separation. A fixed polarizer in the detection instrument is present which aligns perpendicularly to the grating so as to create transverse magnetic mode polarization through the device.

As shown in FIG. 4, if incident light is polarized in an orientation that is between the substrate's two optical axes (a condition that is typically present in the prior art), incident light will experience birefringence as it travels upwards from the bottom substrate surface towards the grating on the top surface in the detector arrangement of FIG. 3. Spatial variation in material properties (optical axis orientation) translates into polarization variability at the grating. Polarization variability at the grating leads to loss of resonance peak uniformity. A similar process occurs as light reflects from the grating back through the substrate.

Figure 5:
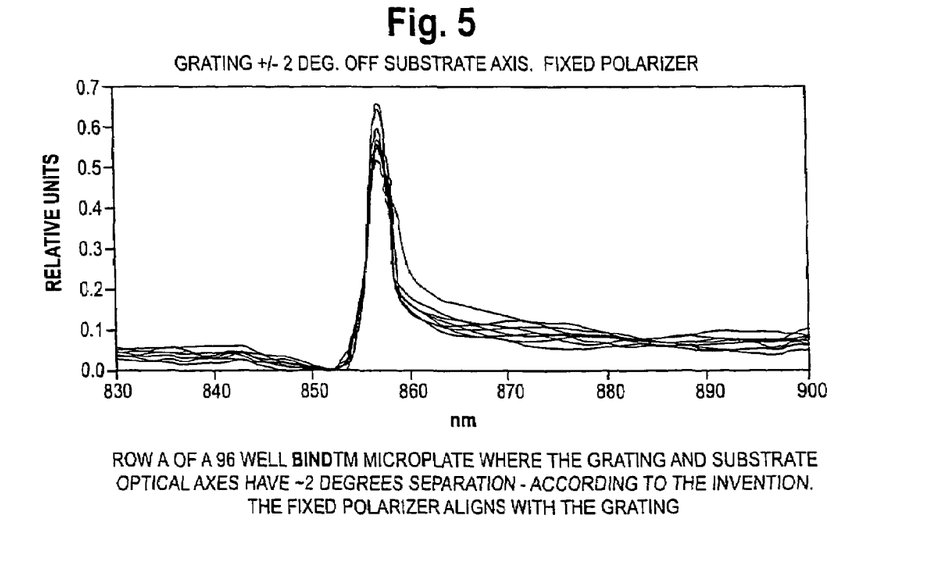
FIG. 5 shows a graph of intensity as a function of wavelength for the same row in the microtiter plate cell where the grating and substrate optical axes are substantially in alignment in accordance with the teachings of this disclosure. In this example, they have ~2 degrees separation. The fixed polarizer aligns perpendicularly to the grating. Note that the resonant frequency peak for all of the unit cells in the row using the construction in which the grating axis and substrate optical axis are aligned is much sharper in FIG. 5 as compared to FIG. 4, resulting in increased accuracy of the detection of the peak wavelength value.

However, as shown in FIG. 5, light polarized in alignment (or close to alignment) with one of the substrates optical axes as explained in this disclosure will not experience birefringence because it "sees" only one refractive index. The result is sharper detected peak resonance frequency and thus increased accuracy with the sensor device.

A presently preferred process of manufacturing biosensors in accordance with the principles of this disclosure will now be explained. The process involves "printing" or replicating the grating onto the substrate. The grating is constructed on the substrate web as explained in the above-cited patent application documents of the applicant's assignee. If the grating X and Y axes align in a parallel and perpendicular manner to the substrate's optical axes (which are also typically at right angles) then the birefringent properties of the substrate do not affect resonance peak quality. Hence, care is taken during manufacturing to correctly orient the grating master wafer relative to the substrate (e.g., by rotating the grating master wafer) such that when the grating is applied to the substrate the desired alignment between grating lines and optical axis is observed.

PET manufacturers typically produce 2M (2 meter) wide rolls or webs of PET film. Optical axis orientation, with respect to the web direction, varies across the width of the web but not in the direction of the web. The 2M roll is cut into smaller rolls, each 0.2M in width. The biosensors are produced from the 0.2M wide rolls. Hence, the process samples many sections across the width of the master roll. This invention compensates for variability in optical axis orientation across the width of the master roll since the measurement of optical axes is made for each 0.2M roll and alignment between grating and optical axes is observed on each 0.2M roll.

In a preferred mode of practicing this invention, a measurement is taken of the orientation of the substrate's two perpendicular optical axes, at the center of the 0.2M web, with respect to the web direction (or web edge). Then, the grating patterning tool (master wafer) is rotated to align the grating with one of the optical axes of the web. In general, it does not matter which axis (fast or slow) the grating aligns with. Typical rotation values range between 0 and 30 degrees at the web's center. The grating is then formed and UV bonded to the substrate web using the grating master wafer. Bonding occurs during UV curing. As the polymer material hardens/crosslinks into the grating shape, it also bonds to the PET substrate. The web is advanced or indexed and another grating is formed and bonded to the web. The web advances and the process repeats. When sensors are constructed as just described, incident light polarized along the second orthogonal axis (basically in a direction extending into the web) maintains its TM orientation when incident on the grating.

The process optimizes alignment at the center of the 0.2M web. Variation from the ideal occurs as the sampling point deviates from the center. However, the effect of birefringence increases approximately as the sine squared of the angle between an optical axis and the incident light polarization. Also the 0.2M web has a relatively small spatial rate of optical axis change across the width of the web. These two points yield the result that optimizing to web center gives excellent resonance peak uniformity over the area of microplate based biosensors.

Beyond improving the uniformity and quality of measured resonance peaks, implementation of the invention has allowed the applicant's assignee to simplify its biosensor reading instrumentation. Before the invention, sensor readers required an adjustable polarizer to partially compensate for polarization rotation induced by the substrate. This apparatus produced usable resonance peaks for substrate rolls with less than ~15 degrees of misalignment between the grating and substrate optical axes. Approximately 40% of the rolls that the assignee uses have optical axes with greater than 15 degrees of angle from the web direction (old grating direction). After making sensors according to this invention, it is possible to make full use of a substrate inventory. Moreover, the prior adjustable polarizer may be replaced with a much simpler fixed polarizer.

Figure 6A:
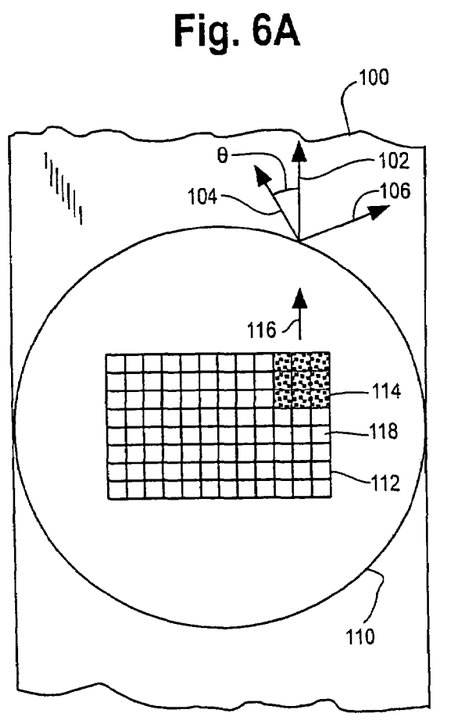
FIGS. 6A and 6B show the arrangement of a grating master wafer and the substrate sheet before, and after, respectively, the alignment of the grating master wafer lines to the optical axis of the substrate material web.

FIG. 6A shows a web 100 of PET film (sensor substrate material) is advanced in a machine direction 102 to a grating station during production of grating-based biosensors of the type described in the above-referenced patent applications of the applicant's assignee. The web 100 is 0.2M in width in this example. The optical axis of the web material is measured beforehand by placing a specimen of the web between crossed polarizers (two polarizers with axes perpendicular to one another) and rotating the web specimen relative to the crossed polarizers to identify the orientation where a photoextinction occurs. The orientation of the web to the crossed polarizers determines the orientation of the optical axes relative to the edges of the web. The fast and slow optical axes of the web specimen are shown as axes 104 and 106, respectively, and are usually perpendicular to one another. The axis 104 is offset from the direction of the web movement (and the edge of the web) by angle θ. Note that in FIG. 6A, the axis 116 is aligned with the web direction of travel 102 instead of the optical axis 104 or 106, a situation which is corrected in this invention. A roll (not shown) is applied to the web 100 and rolls the web over a silicon wafer grating master 100. The master forms a rating 112 of UV cured material on the web 100. The grating 112 consists of a periodic surface of low index of refraction material arranged in a plurality of rows and columns of units (or cells), each of which has a multitude of grating elements 114 of the type shown in FIG. 1 as reference 12. The rectangular arrangement of the grating elements defines lines having a grating axis shown as 116.

Figure 6B:
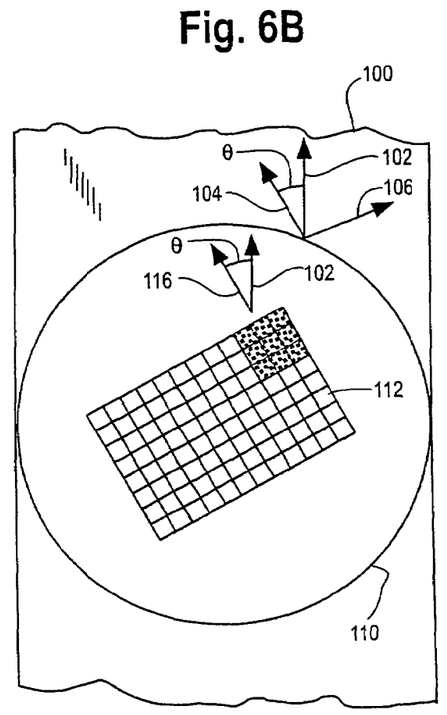

As shown in FIG. 6B, manufacture of the biosensor at the grating station is designed such that alignment is specified between the grating axis 116 and the optical axis 104 (or 106) of the web substrate 100. To achieve this, the master grating wafer 110 is rotated by an amount such that the grating axis 116 and the optical axis 104 are substantially aligned with each other (preferably within a few degrees of each other). A UV curable material (e.g., liquid epoxy) is applied in droplet form to the wafer grating master 110, the material is spread using pressure from the roller behind the web 100, and then the material is UV cured to form and bond the grating pattern 112 onto the PET web 100. This arrangement of the master 110 and grating 112 relative to the web 100 is shown in FIG. 6B. Exact alignment of the two axes is not required, but closer alignment is better. Now, both the optical axis 104 and the grating axis 116 form the same angle θ relative to the direction 102 of travel of the web. The web is advanced, the cured epoxy grating+web is peeled away from the master grating wafer 110, another grating is applied to the web 100 using the master grating wafer 110 as described above, and the process repeats in a continuous fashion.

In a downstream station (not show), high index of refraction material is deposited on the grating, and the grating 112 is cut from the web 100. The grating is then bonded to the bottom of a 96 well bottomless microtitre plate with the individual cells 118 aligned with the individual wells of the microtitre plate. The biosensor device is then ready for use e.g., with a detection instrument as described in the above-referenced patent applications.

While a number of exemplary aspects and embodiments have been discussed above, those of skill in the art will recognize certain modifications, permutations, additions and sub-combinations thereof. For example, other tools or processes may be used to form a grating on a substrate material than those described herein without departure from the scope of this invention. It is therefore intended that claims hereafter introduced are interpreted to include all such modifications, permutations, additions and sub-combinations as are within their true spirit and scope.

I claim:

1. A biosensor comprising:
    a substrate, the substrate comprising a birefringent material having two optical axes; and
    a grating applied to the substrate,
    wherein the grating comprises features arranged in a plurality of parallel lines and wherein the lines of the grating are in substantial alignment with one of the optical axes of the substrate; wherein the grating comprises a UV-curable material applied to the substrate using a grating master wafer.

2. The biosensor of claim 1, wherein the substrate comprises a clear polymer film.

3. The biosensor of claim 2, wherein the film comprises a polyethylene terepthalate (PET) film.

4. A method of manufacturing a biosensor, comprising the steps of:
    a) feeding a web of birefringent substrate material to a station, the web of substrate material having two optical axes;
    b) applying a grating to the substrate material at the station, wherein the grating comprises a plurality of parallel lines;
        wherein, in the performance of step (b), the grating is applied to the substrate in a manner whereby the lines of the grating are in substantial alignment with one of the optical axes of the web of substrate material;
    c) determining an optical axis orientation of the web of substrate material, and, before or during the performance of step b) orienting a grating wafer for use in applying the grating to the substrate material relative to the substrate whereby the grating wafer is oriented in substantial alignment with the optical axis orientation;
        wherein the grating is formed of a UV curable material.

5. The method of claim 4, wherein the substrate material comprises a clear polymer film.

6. The method of claim 5, wherein the clear polymer film comprises a polyethylene terepthalate (PET) film.

7. The method of claim 4, wherein the step of determining the optical axis orientation is performed at substantially the center of the web of material.

8. A method of manufacturing a biosensor, comprising the steps of:
    a) feeding a web of birefringent substrate material to a station, the web of substrate material having two optical axes;
    b) applying a grating to the substrate material at the station, wherein the grating comprises a plurality of parallel lines;
        wherein, in the performance of step (b), the grating is applied to the substrate in a manner whereby the lines of the grating are in substantial alignment with one of the optical axes of the web of substrate material;
        wherein the method is performed substantially continuously on a continuous web of substrate material.

9. The method of claim 8, wherein the continuous web of substrate material is formed by dividing a master web of substrate material into a plurality of continuous longitudinal strips, each strip forming a continuous web of substrate material.

10. A method of manufacturing a biosensor, comprising the steps of:
    a) providing a continuous web of substrate material;
    b) determining the orientation of an optical axis in the web of substrate material;
    c) providing a grating master wafer having a plurality of parallel lines;

d) orienting the grating master wafer relative to the web of substrate material such that the lines of the grating master wafer are in substantial alignment with the optical axis;
e) forming a grating on the web of material using the grating master wafer; and
f) advancing the web of substrate material relative to the grating master wafer and repeating step e).

11. The method of claim 10, wherein the grating is formed of a UV curable material.

12. The method of claim 10, wherein the substrate material comprises a clear polymer film.

13. The method of claim 12, wherein the clear polymer film comprises a polyethylene terepthalate (PET) film.

* * * * *

UNITED STATES PATENT AND TRADEMARK OFFICE
CERTIFICATE OF CORRECTION

| | |
|---|---|
| PATENT NO. | : 7,162,125 B1 |
| APPLICATION NO. | : 11/207442 |
| DATED | : January 9, 2007 |
| INVENTOR(S) | : Schulz et al. |

Page 1 of 1

It is certified that error appears in the above-identified patent and that said Letters Patent is hereby corrected as shown below:

Col. 1, Line 59, "calorimetric" should read --colorimetric--.

Signed and Sealed this

Thirtieth Day of September, 2008

JON W. DUDAS
*Director of the United States Patent and Trademark Office*